United States Patent
Scotto et al.

(12)

(10) Patent No.: US 11,186,542 B2
(45) Date of Patent: Nov. 30, 2021

(54) COMBINED APPARATUS FOR THE SYNTHESIS OF UREA

(71) Applicant: Casale SA, Lugano (CH)

(72) Inventors: Andrea Scotto, Breganzona (CH); Enrico Rizzi, Casnate con Bernate (IT)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 15/780,552

(22) PCT Filed: Jan. 31, 2017

(86) PCT No.: PCT/EP2017/052019
§ 371 (c)(1),
(2) Date: May 31, 2018

(87) PCT Pub. No.: WO2017/157561
PCT Pub. Date: Sep. 21, 2017

(65) Prior Publication Data
US 2019/0002401 A1    Jan. 3, 2019

(30) Foreign Application Priority Data

Mar. 17, 2016    (EP) .................................. 16160846

(51) Int. Cl.
*B01J 19/00*    (2006.01)
*B01J 19/24*    (2006.01)
(Continued)

(52) U.S. Cl.
CPC ............ *C07C 273/04* (2013.01); *B01D 3/009* (2013.01); *B01D 5/006* (2013.01); *B01D 5/0015* (2013.01); *B01J 19/006* (2013.01); *B01J 19/0053* (2013.01); *B01J 19/244* (2013.01); *B01J 19/0013* (2013.01); *B01J 2219/00078* (2013.01);
(Continued)

(58) Field of Classification Search
CPC ... C07C 273/04; B01J 19/2455; B01J 19/246; B01J 2219/00078
See application file for complete search history.

(56) References Cited

U.S. PATENT DOCUMENTS 2,800,307 A * 7/1957 Putney ...................... F28D 7/06
159/901
3,027,242 A * 3/1962 Webb, Jr. ............. B01J 19/2425
422/200
3,446,601 A * 5/1969 Ma .......................... B01J 3/042
422/200
(Continued)

FOREIGN PATENT DOCUMENTS

| FR | 958503 A | * | 3/1950 | ........... C07C 273/04 |
| GB | 1031528 A | * | 6/1966 | ........... C07C 273/04 |
| WO | 00/43358 A1 | | 7/2000 | |

OTHER PUBLICATIONS

Machine translation of FR 958503 A (Mar. 1950). Retrieved from EPO website on Sep. 4, 2019. (Year: 2019).*
(Continued)

*Primary Examiner* — Jennifer A Leung
(74) *Attorney, Agent, or Firm* — Akerman LLP

(57) ABSTRACT

Combined apparatus (1) for the synthesis of urea from ammonia and carbon dioxide, comprising an internal wall (3) which delimits two coaxial zones (4) inside the apparatus, operating respectively as reaction (4) and condensation (5) zones, and optionally also comprising a stripping zone and/or a scrubber integrated in the same apparatus.

9 Claims, 4 Drawing Sheets

(51) Int. Cl.
*C07C 273/04* (2006.01)
*B01D 3/00* (2006.01)
*B01D 5/00* (2006.01)
*C07C 273/16* (2006.01)

(52) U.S. Cl.
CPC ........... *B01J 2219/00081* (2013.01); *B01J 2219/00108* (2013.01); *B01J 2219/00159* (2013.01); *B01J 2219/00768* (2013.01); *B01J 2219/00777* (2013.01); *B01J 2219/1943* (2013.01); *C07C 273/16* (2013.01); *Y02P 20/141* (2015.11)

(56) References Cited

U.S. PATENT DOCUMENTS

| | | | | |
|---|---|---|---|---|
| 3,932,504 A * | 1/1976 | Chen | ............ | B01J 3/04 564/71 |
| 6,680,407 B2 * | 1/2004 | Mennen | ............ | B01J 3/04 422/149 |
| 2006/0099118 A1 * | 5/2006 | Filippi | ............ | B01J 19/0013 422/148 |
| 2009/0062566 A1 * | 3/2009 | Kojima | ............ | B01D 3/343 564/67 |

OTHER PUBLICATIONS

International Search Report issued in connection with PCT/EP2017/052019.
International Preliminary Report on Patentability issued in connection with PCT/EP2017/052019.

* cited by examiner

COMBINED APPARATUS FOR THE SYNTHESIS OF UREA

This application is a national phase of PCT/EP2017/052019, filed Jan. 31, 2017, and claims priority to EP 16160846.8, filed Mar. 17, 2016, the entire contents of both of which are hereby incorporated by reference.

FIELD OF APPLICATION

The invention relates to a combined apparatus for high-pressure urea synthesis.

PRIOR ART

Processes and apparatuses for the synthesis of urea from ammonia and carbon dioxide are known and described in literature, for example in Meessen, "Urea", Ulmann's Encyclopedia of Industrial Chemistry, Wiley-VCH Verlag, 2010.

The reaction between ammonia and carbon dioxide is performed in a reactor and comprises a first highly exothermic stage producing ammonium carbamate and a second endothermic stage converting the ammonium carbamate into urea and water.

The reactor produces an aqueous solution essentially containing urea, unconverted ammonium carbamate and free ammonia, and a gaseous mixture containing ammonia, carbon dioxide and possible inert gases.

Most of the urea plants operate using the stripping process wherein the aqueous solution leaving the reactor is sent to a stripper where the carbamate is decomposed into ammonia and carbon dioxide. The stripping process is assisted by a heat supply and, in $CO_2$ stripping plants, by a flow of carbon dioxide acting as stripping agent for separating the gaseous phase (consisting mainly of ammonia and carbon dioxide) from the liquid phase.

The stripping process consequently produces a more concentrated aqueous solution of urea and a gas flow containing ammonia and carbon dioxide. The aqueous solution is generally conveyed to a treatment section at lower pressure; the gases are at least partly condensed inside a specific condenser and the so obtained condensate is recirculated back to the reactor.

The gaseous mixture extracted from the reactor is also transformed into carbamate inside a scrubber.

The mentioned apparatuses, i.e. the reactor, the stripper, the condenser and the scrubber, substantially operate at the same pressure and form the so called synthesis loop or high-pressure loop.

The presence of four separate apparatuses, each one having its own pressurized vessel, constitutes a high cost. All these apparatuses operate under strict operating conditions (high pressure and temperature) and with highly corrosive fluids, therefore requiring high-quality materials and complex constructional solutions. In addition, each apparatus requires respective foundations; the pipes for connecting together the apparatuses require high-quality material and are costly.

In an attempt to reduce these costs, the prior art has proposed the combination of the reactor and the condenser within a single combined apparatus.

The combined apparatuses of the prior art, constructed for this purpose, are essentially formed by a vertical cylindrical body comprising a reactor section and a tube bundle condenser section which are vertically arranged one above the other, the condenser section being generally located underneath the reactor section.

Such an embodiment, however, is not satisfactory because the condenser requires a tube bundle integrated in the apparatus and substantially having the same diameter as the vessel. This gives rise to a number of drawbacks: the tube plates are difficult to manufacture beyond a certain diameter and this factor limits the maximum size and therefore the maximum capacity of the reactor; the replacement of damaged pipes becomes a very complex operation and requires a long downtime of the plant, because the tube bundle is integrated inside the reactor; because of the different thermal expansion between vessel and tubes, the vessel must be provided with flexible corrugated sections, which are costly. The apparatus has a considerable height since the sections are situated one above the other and consequently it is difficult to transport and install.

For example, WO 00/43358 describes a combined apparatus which performs the functions of reactor, condenser and scrubber.

SUMMARY OF THE INVENTION

The invention aims to overcome the abovementioned problems and limitations of the prior art. In greater detail, the invention proposes to provide a combined reactor which is able to combine the functions of reactor and condenser and which allows the following advantages to be achieved compared to the prior art: greater productive capacity, less complex design, ease of extraction and replacement of the damaged heat exchange elements, reduction of the costs for the reactor construction and maintenance.

These objects are achieved with a combined apparatus for the synthesis of urea from ammonia and carbon dioxide, comprising a shell and comprising a reaction zone and a condensation zone, communicating with each other and contained within said vessel, characterized in that one of said reaction and condensation zones is arranged coaxially the outside of the other zone.

Further preferred aspects of the invention are described in the dependent claims.

Preferably one of said reaction and condensation zones has a cylindrical or substantially cylindrical geometry and the other of said two zones has an annular or substantially annular geometry.

In a preferred embodiment, the apparatus comprises an additional internal wall delimiting said reaction and condensation zones inside the apparatus.

An apparatus according to the invention may be called combined reactor-condenser. The apparatus comprises a first region and a second region, which are coaxial with each other. One of said regions extends coaxially around the other. According to different embodiments of the invention, the first region may operate as reactor and the second region as condenser or vice versa. In the first case the combined apparatus of the invention may be defined as central reactor; in the second case, on the other hand, it may be defined as central condenser.

The term "reaction zone" is understood as meaning a region of the apparatus wherein the reactions of urea formation, i.e. more precisely formation of ammonium carbamate and conversion of carbamate into urea and water, mainly take place. The term "condensation zone" is understood as meaning a region of the apparatus wherein heat is removed and condensation of the ammonia and $CO_2$ vapours mainly takes place. The heat removed from the condenser represents the condensation heat of the ammonium carbamate. According to some embodiments of the invention, part of the urea formation reaction may take place in the condensation zone.

In a particular embodiment, of the central condenser type, the condensation zone is formed by a bottom portion of a cylindrical or substantially cylindrical region on the inside of an additional wall, and the reaction zone comprises a top portion of said region on the inside of the additional wall, above the condensation zone, as well as an annular or substantially annular region extending around the additional wall. In this embodiment, the central region of the apparatus, on the inside of the additional wall, comprises the condensation zone and also part of the reaction zone.

Preferably, the condensation zone receives ammonia and $CO_2$ vapours from a stripping process of an aqueous solution of urea containing unconverted carbamate.

Cooling elements are advantageously installed in the condensation zone, which are designed to remove condensation heat and are passed through by a cooling fluid, for example evaporating water. The heat exchange elements are for example formed by tubes or plates. According to a first preferred embodiment, a bayonet tube bundle with a single tube plate is provided. In another preferred embodiment a U-tube bundle is provided.

The apparatus according to the invention may be connected to an external stripper and, where envisaged, to a scrubber. For example, an aqueous solution of urea extracted from the apparatus is supplied to a stripper and the vapours from the stripper, mainly formed by ammonia and CO2, are supplied to the reaction zone of the apparatus. The carbamate solution from the scrubber is also supplied to the reaction zone. The apparatus may comprise, for this purpose, a suitable distributor, preferably arranged in the lowest part or on the bottom of the reaction zone.

In some embodiments the apparatus of the invention may also comprise an integrated stripper and/or scrubber.

A stripping zone, where envisaged, is preferably situated in the lowest part of the apparatus, i.e. underneath the coaxial reaction and condensation zones.

The stripping zone is preferably supplied with a stripping agent, even more preferably formed by gaseous CO2.

A scrubbing zone, when envisaged, is advantageously situated in the top part of the apparatus above the coaxial reaction and condensation zones.

A first advantage of the invention consists in the compactness of the apparatus. Owing to the coaxial arrangement, the apparatus according to the invention is smaller and easier to transport and install compared to the column reactors-condensers of the prior art. Moreover, the combined apparatus is easier to transport and to install with respect to the plurality of apparatuses which it replaces.

Another advantage of the invention is that the heat exchange elements may be produced at a lower cost than conventional tube bundles. For example they can be realized with bayonet tubes or U-tubes which require a single tube plate. The embodiments with central condenser have the further advantage that the heat exchange elements are grouped together within a relatively small diameter in the centre of the apparatus: for example a tube bundle has a smaller and, therefore, less costly tube plate.

The use of bayonet tubes results in further advantages owing to the single-plate configuration: the disassembly and/or replacement of the tubes is simplified and does not require long downtimes of the plant. The plate and tubes assembly can be easily extracted from the reactor since the tubes are fixed to a single plate. Moreover, the bayonet tubes have a free end (on the opposite side of the tube plate) and therefore are free to expand; this means that the different expansion of the tubes compared to the vessel does not produce tension and does not require special compensation devices. This advantage is also obtained with a U-tube bundle.

Another advantage consists in the substantially axial symmetry which ensures uniform conditions inside the reactor. This is advantageous in a complex reaction such as the synthesis of urea and ensures to suitably use the entire volume available inside the apparatus.

The invention also relates to a process for the synthesis of urea from ammonia and carbon dioxide according to the accompanying claims.

The detailed description which follows relates to preferred embodiments, which are described by way of a non-limiting example.

DETAILED DESCRIPTION

Figure 1:
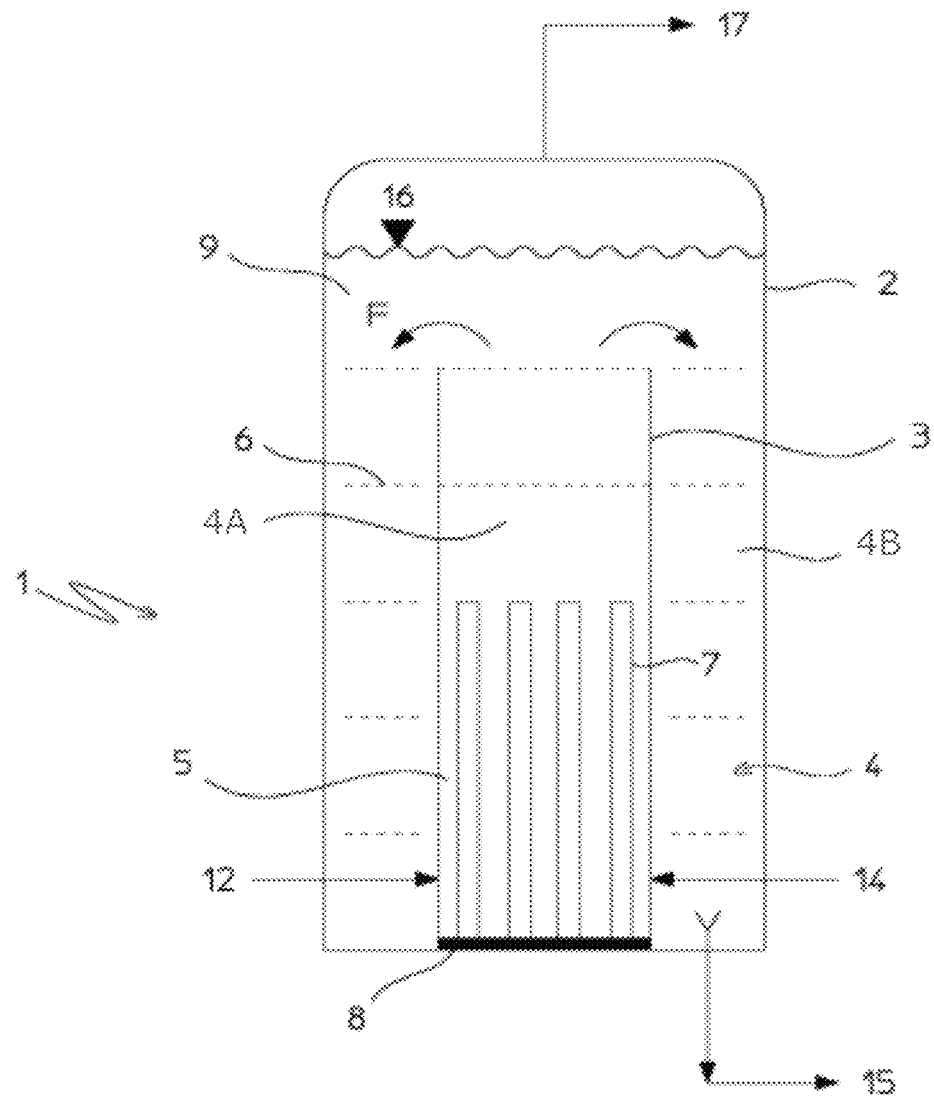
FIG. 1 is a schematic cross-sectional view of a combined reactor for the synthesis of urea, according to a first embodiment of the invention.

FIG. 1 shows a combined reactor-condenser apparatus 1 according to an embodiment of the invention of the central condenser type. Said reactor-condenser 1, for example, forms part of a high-pressure loop which also comprises a stripper and a scrubber.

The combined reactor-condenser 1 comprises an external shell 2 and an additional internal wall 3 which is also termed internal shell and is preferably a cylindrical wall. The external shell 2 and the internal shell 3 define separate zones inside the apparatus 1 and in particular define a reaction zone 4 and a condensation zone 5.

The condensation zone 5 is formed by at least a part of the substantially cylindrical volume on the inside of the wall 3. In the example according to FIG. 1 the condensation zone 5 is essentially formed by the lowest part of said cylindrical volume.

The reaction zone comprises the volume extending around the wall 3 and optionally also a part of the volume on the inside of said wall. In the example shown in FIG. 1 the reaction zone 4 comprises a first portion 4A on the inside of the wall 3 and above the condensation zone 5, as well as a second portion 4B formed by a region having annular or substantially annular geometry which extends around the wall 3, for example said second portion 4B of the reaction zone 4 being defined between the wall 3 and the shell 2 of the apparatus 1.

The reaction zone 4 contains perforated plates 6 which divide said reaction zone into compartments according to per se known art in the field of urea reactors. The plates 6 are substantially in the form of disks in the first portion 4A, while they are substantially rings in the second portion 4B, in accordance with the geometry of said two portions of the reaction zone.

The condensation zone 5 contains heat exchange elements in the form of bayonet tubes 7 mounted on a tube plate 8.

Said tubes 7 are supplied with a cooling fluid such as water, and remove heat from the zone 5 allowing the desired condensation process to take place.

In FIG. 1 the tube plate 8 is located on the bottom of the apparatus 1, at the bottom end of the tubes. In an alternative embodiment, said tube plate 8 may be situated at the top end of the tubes.

FIG. 1 shows a preferred embodiment wherein the condensation zone 5 is in the centre of the apparatus (central condenser) and is bounded by the internal shell 3. Consequently, the diameter of the tube plate 8 is substantially smaller than the diameter of the external shell 2, i.e. than the nominal diameter of the apparatus 1 (for example the diameter of the plate 8 is about half the diameter of the shell 2). This is an advantage because the tube plate 8 is a relatively costly component.

The reactor 1 has a top portion 9, above the top of the internal shell 3, which allows communication between the coaxial zones 4 and 5 and in particular allows the second region 4B of the reaction zone 4 to be supplied with the condensate produced in the condensation zone 5 (through the first region 4A) similarly to a conventional plant where the effluent of the condenser feeds the reactor.

The inputs of the apparatus 1 are formed by a flow 12 containing ammonia and $CO_2$ in gaseous form and by a recovery solution 14 comprising ammonium carbamate and supplied from an external scrubber. Preferably said feeding flows 12 and 14 are directly introduced into the condensation zone 5 (through suitable inlet flanges and pipes) as shown schematically in the figures.

The apparatus 1 produces an aqueous solution 15 containing urea, carbamate and ammonia, which substantially corresponds to the effluent of a conventional urea reactor and which is supplied to the already mentioned external stripper. Said external stripper in turn produces a more concentrated solution and the flow of vapours 12 which returns to the apparatus 1. Advantageously, the solution 15 is removed from the bottom of the second region 4B (annular region) of the reaction zone 4.

In normal operating conditions the reactor 1 is almost completely full with an aqueous urea solution, as indicated by the level 16.

The line 17 represents a gaseous phase (head gas) which is extracted from the top end of the reactor-condenser 1 and is generally supplied to an external scrubber.

The arrows F indicate the flow which, rising up on the inside of the wall 3, passes from the condensation zone 5, and from the first portion 4A of the reaction zone 4, to the second portion 4B of the reaction zone 4. In the example, the flow F has a substantially ascending motion inside the central duct defined by the internal shell 3 and flows out into the already described annular region forming the portion 4B of the reaction zone.

Figure 2:
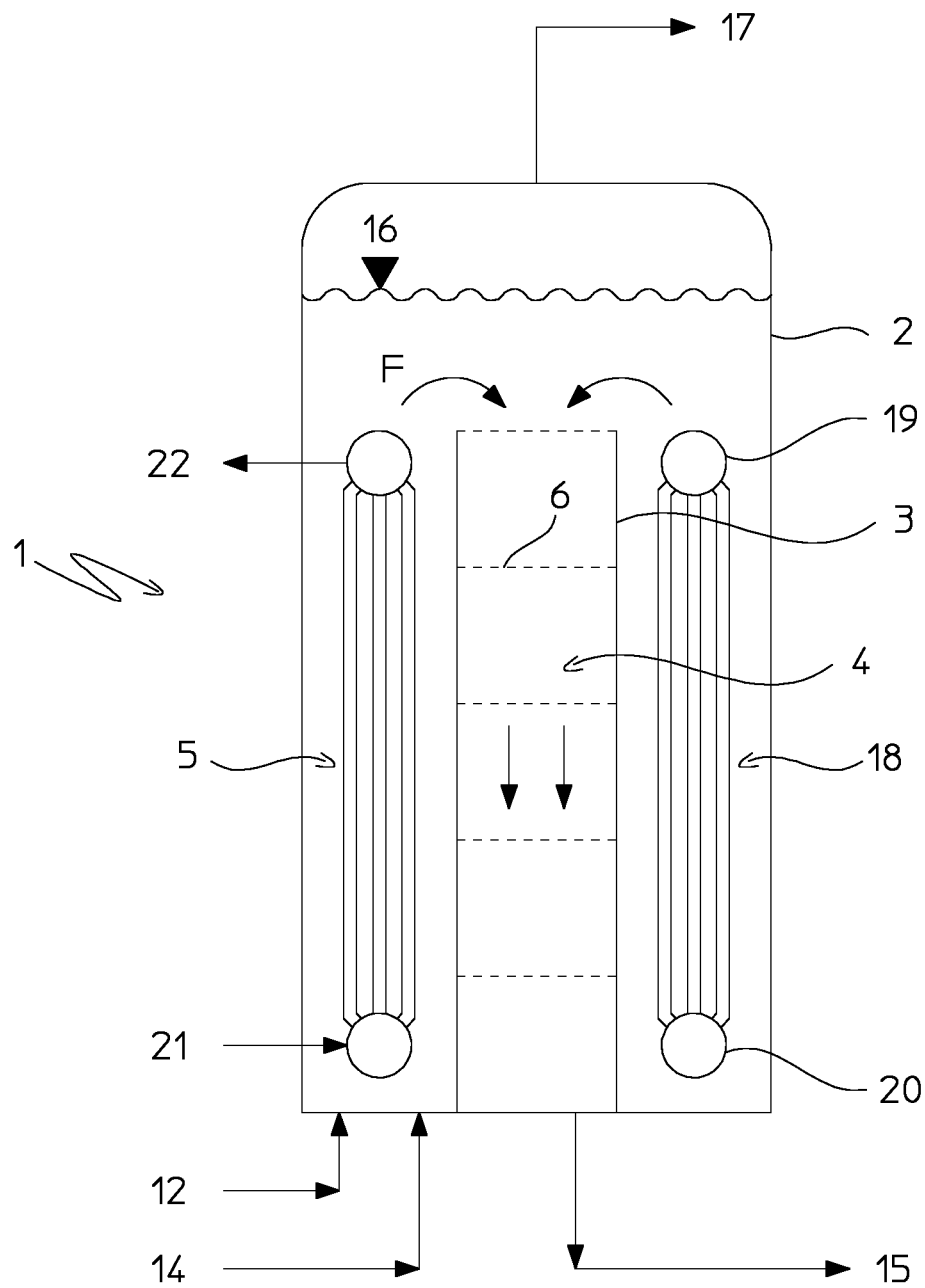
FIG. 2 is a schematic cross-sectional view of a combined reactor for the synthesis of urea, according to another embodiment of the invention.

FIG. 2 shows an embodiment of the central reactor type. In this embodiment, the condensation zone 5 extends coaxially around the reaction zone 4. The embodiment of FIG. 2, therefore, can be regarded as dual with respect to that shown in FIG. 1. The reaction zone 4 is substantially cylindrical, while the condensation zone 5 is substantially annular.

The reference numbers in FIG. 2 correspond to those shown in FIG. 1 and the description is not repeated for the sake of brevity. FIG. 2 shows a preferred embodiment which comprises a tube bundle 18 intended to cool the condensation zone 5. Said tube bundle 18 comprises a top header 19 and a bottom header 20; it is supplied with water 21 and produces steam 22.

The arrows in FIG. 2 indicate the flow of the urea solution which passes from the condensation zone 5 into the reaction zone 4 and which has a descending motion inside said reaction zone 4, i.e. on the inside of the wall 3.

The embodiments with bayonet tubes (as in FIG. 1), with U-tubes, or with headers (as in FIG. 2), can be applied in an equivalent manner to apparatuses of the central reactor or central condenser type. Moreover, in all the embodiments of the invention, plates can be used instead of tubes as heat exchange elements.

For example, in a central condenser embodiment, such as that shown in FIG. 1, it is possible to provide a set of plates in the condensation zone 5, on the inside of the wall 3. In a central reactor embodiment, such as that shown in FIG. 2, it is possible to provide radially distributed plates within the condensation zone 5.

It should be noted that the embodiments shown in FIG. 1 and FIG. 2 have the same interface towards the external environment. In both cases, the apparatus 1 receives the flow 12 of ammonia and $CO_2$ and the solution containing carbamate 14, and exports the aqueous solution of urea 15 and the head gases 17.

Figure 3:
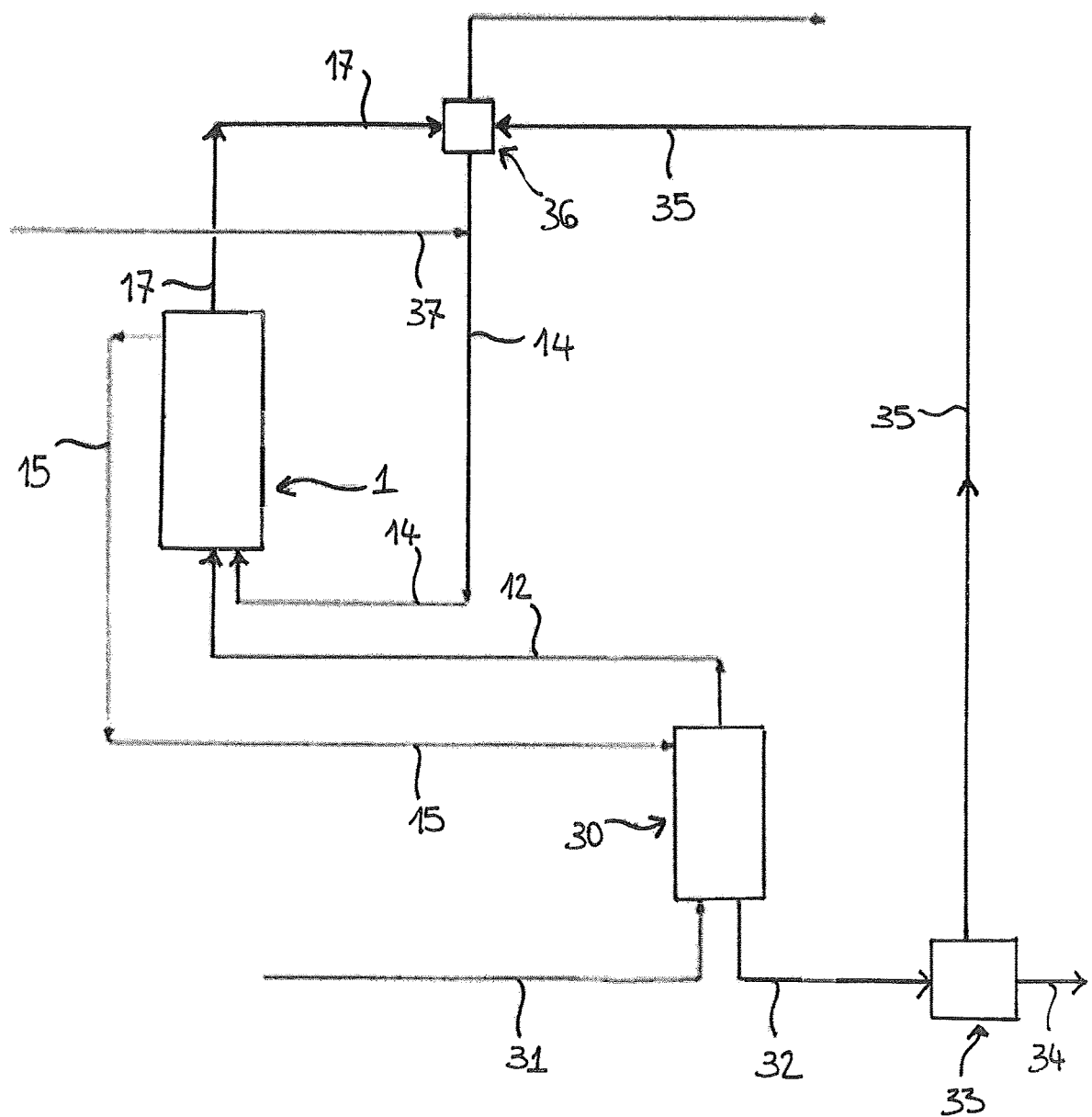
FIG. 3 is a simplified diagram of a plant comprising the combined reactor according to FIG. 1 or FIG. 2.

FIG. 3 shows an example of the apparatus 1 of FIGS. 1-2 inserted in a high-pressure urea synthesis loop.

The aqueous solution 15 produced inside the reactor-condenser 1, essentially comprising urea, ammonium carbamate and free ammonia, is fed to a stripper 30, which is supplied from below with a stream of carbon dioxide 31 as stripping agent. The stripper 30 is for example a shell and tube bundle apparatus heated by a flow of steam.

The gaseous stream 12 extracted from the top of the stripper, essentially ammonia and carbon dioxide, is conveyed to the reactor 1. The solution 32 leaving the stripper, essentially comprising urea, residual ammonium carbamate and ammonia, is conveyed to a recovery section 33 according to the known art. The recovery section provides a urea concentrated solution 34 and a flow of carbamate 35.

Said flow of carbamate 35 is supplied to a scrubber 36, together with the gases 17 extracted from the reactor-condenser 1. Said scrubber 36 produces the flow 14 which, as mentioned above, is supplied to the reactor-condenser 1, for example together with fresh ammonia 37.

Figure 4:
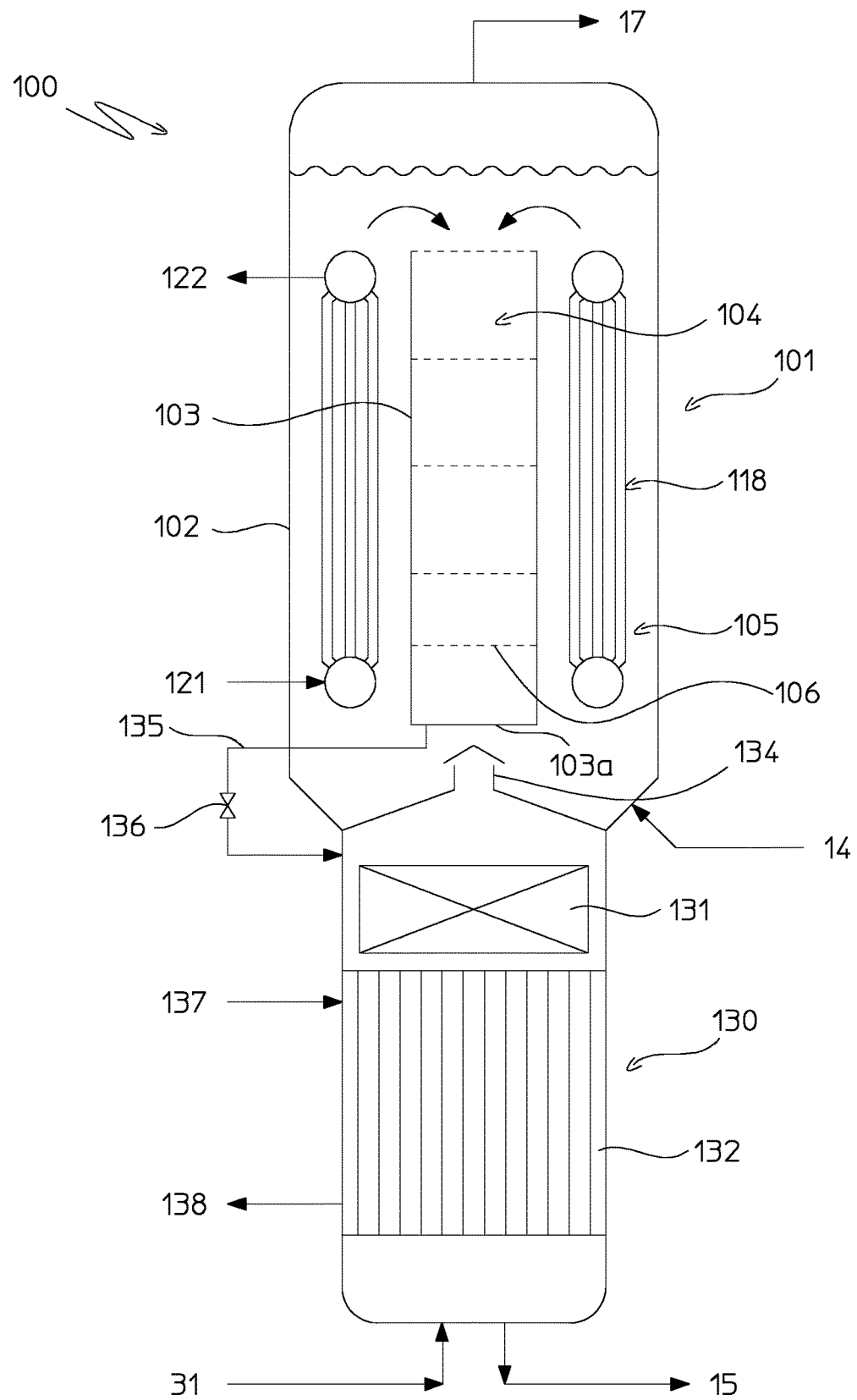
FIG. 4 is a schematic cross-sectional view of a combined reactor for the synthesis of urea, according to another embodiment which also provides for a stripper section integrated in the apparatus.

FIG. 4 shows a further variant of the invention, formed by an apparatus 100 which comprises coaxial sections of reaction and condensation, and also comprises a stripping section.

The apparatus 100, in greater detail, comprises a top section 101 which operates as a reactor-condenser and a bottom section 130 which operates as a stripper.

The top section 101 can be realized as shown in FIG. 1 (central condenser) or as shown in FIG. 2 (central reactor). In the example shown in FIG. 4, the section 101 reflects the embodiment shown in FIG. 2 comprising a central reaction zone 104 and an annular condensation zone 105. Said zones 104 and 105 are bounded by an external shell 102 and by an additional internal wall (internal shell) 103. The bottom part 103a of the shell 103 is sealed so that the zones 104 and 105 communicate only in the top part of the apparatus in order to prevent mixing of products and reagents. Plates 106 are installed in the reaction zone 104. A tube bundle 118 supplied with water 121 and producing steam 122 (similarly to FIG. 2) is present in the condensation zone 105.

In this example, the stripping section 130 is of the $CO_2$-stripping type and essentially comprises a liquid distributor 131, a tube bundle 132 and a line 31 which supplies gaseous $CO_2$ as stripping agent.

The stripping section 130 communicates with the top section 101 through a flue 134 and a suitable hydraulic guard. Said flue 134 allows the gaseous phase, exiting the stripping section 130, to pass into the overlying condensation section 105 and the hydraulic guard prevents a flow of liquid backwards.

A line 135 with a reactor level control valve 136 supplies the aqueous solution of urea from the reaction section 105 to the stripping section 130, in particular to the tube side of the bundle 132.

The shell side of the tube bundle 132 is heated with steam 137 and the cooled or condensed steam is extracted via the line 138. In some embodiments, the steam 137 can be produced, wholly or partly, inside the bundle 118 which cools the condensation zone 105 of the same apparatus 100. For example, in some embodiments, at least part of the flow of steam 122 forms said heating steam 137. In other embodiments, the steam 137 is supplied from the outside.

The operating principle of the combined apparatus 100 is now described in brief. The aqueous solution produced in the reaction zone 104 descends inside the tubes of the bundle 132 where it comes into contact, in counterflow, with the stripping $CO_2$ 31 supplied from below. A liquid film adhering to the walls (falling film) is formed inside the tubes. The heat necessary for decomposition of the ammonium carbamate contained in the urea solution is supplied by the steam 137 circulating in the shell side of the stripping section 130. The liquid phase is collected on the bottom of the apparatus and forms the flow of concentrated solution 32; the gaseous flow exiting the stripper passes into the condensation section 105; the condensate formed in said zone 105 subsequently passes into the reaction zone 104.

The apparatus 100 can be inserted in a layout such as that shown in FIG. 4 where the apparatus 100 replaces both the reactor-condenser 1 and the stripper 30. The combined apparatus 1 receives a recovery solution from a scrubber (preferably with the addition of fresh ammonia) as well as the gaseous stripping $CO_2$, and exports the concentrated urea solution and the head gases.

For example, with reference to the layout shown in FIG. 4, the apparatus 100 can be inserted so as to receive the solution 14 coming from the scrubber 36 and added with ammonia 37, as well as the flow 31 of gaseous $CO_2$; the output of the apparatus 100, instead, comprises the concentrated urea solution 32 which is directed towards the recovery section 33, and the head gases 17 which are directed towards the scrubber 36.

In a further embodiment (not shown) the combined apparatus 1 (FIG. 1-2) or 100 (FIG. 4) comprises a further head section which operates as a scrubber. Said scrubber section is situated above the coaxial reaction and condensation sections, receives the vapours 17 and returns the solution 14. Basically, with this further embodiment the scrubber 36 of FIG. 3 is also integrated in a single apparatus.

What is claimed is:

1. A combined apparatus for the synthesis of urea from ammonia and carbon dioxide, comprising a shell and comprising a reaction zone and a condensation zone, said two zones communicating with each other and being contained inside said shell,
    wherein said reaction zone is arranged coaxially outside of said condensation zone;
    wherein cooling elements are arranged in the condensation zone,
    wherein said cooling elements comprise a tube bundle having a tube plate; and
    wherein the condensation zone is defined in a central region of the apparatus, and the tube plate has a substantially smaller diameter than the diameter of the shell of said apparatus.

2. The apparatus according to claim 1, wherein said condensation zone has a cylindrical or substantially cylindrical geometry and said reaction zone has an annular or substantially annular geometry, extending around said condensation zone.

3. The apparatus according to claim 1, comprising an additional internal wall which delimits said reaction and condensation zones inside the apparatus.

4. The apparatus according to claim 3, wherein:
    said condensation zone comprises a cylindrical or substantially cylindrical region which is located on the inside of said additional wall, and
    said reaction zone comprises an annular or substantially annular region which extends externally around said additional wall.

5. The apparatus according to claim 4, wherein:
    the condensation zone is represented by a bottom portion of said cylindrical or substantially cylindrical region on the inside of the additional wall, and
    the reaction zone comprises a top portion of said region on the inside of the additional wall, above the condensation zone, as well as the annular or substantially annular region which extends around the additional wall.

6. The apparatus according to claim 3, wherein the reaction zone, having annular or substantially annular geometry, is defined between said additional wall and said shell of the apparatus.

7. The apparatus according to claim 1, wherein the tubes are bayonet tubes and said tube bundle has a single tube plate.

8. The apparatus according to claim 1, also comprising a stripping zone and/or a scrubbing zone integrated into said apparatus.

9. The apparatus according to claim 8, comprising:
    a top section which comprises said coaxial reaction and condensation zones, and optionally the scrubbing zone; and
    a bottom section which comprises the stripping zone.

* * * * *